US009238239B2

(12) United States Patent
Adams et al.

(10) Patent No.: US 9,238,239 B2
(45) Date of Patent: Jan. 19, 2016

(54) ATOMIZING STERILIZATION OF A PLURALITY OF CLEANING AGENTS

(75) Inventors: Michael B. Adams, Layton, UT (US); Jeffrey S. Evans, Kaysville, UT (US); David E. Gillies, Farmington, UT (US)

(73) Assignee: Pure Maintenance, Bountiful, UT (US)

( * ) Notice: Subject to any disclaimer, the term of this patent is extended or adjusted under 35 U.S.C. 154(b) by 725 days.

(21) Appl. No.: 13/492,157

(22) Filed: Jun. 8, 2012

(65) Prior Publication Data

US 2013/0140374 A1    Jun. 6, 2013

Related U.S. Application Data

(60) Provisional application No. 61/494,790, filed on Jun. 8, 2011.

(51) Int. Cl.
| | | |
|---|---|---|
| *B05B 17/00* | (2006.01) | |
| *B05B 7/04* | (2006.01) | |
| *B05B 7/24* | (2006.01) | |
| *B05B 7/08* | (2006.01) | |
| *B05B 12/00* | (2006.01) | |
| *E01H 13/00* | (2006.01) | |
| *A01G 25/16* | (2006.01) | |
| *A01G 25/09* | (2006.01) | |
| *A61L 2/18* | (2006.01) | |
| *B05B 12/04* | (2006.01) | |

(52) U.S. Cl.
CPC ............ *B05B 7/0408* (2013.01); *A01G 25/09* (2013.01); *A01G 25/16* (2013.01); *A61L 2/18* (2013.01); *B05B 7/04* (2013.01); *B05B 7/0416* (2013.01); *B05B 7/08* (2013.01); *B05B 7/0815* (2013.01); *B05B 7/2472* (2013.01); *B05B 12/00* (2013.01); *B05B 12/04* (2013.01); *E01H 13/00* (2013.01)

(58) Field of Classification Search
CPC ...... B05B 7/08; B05B 7/0815; B05B 7/2472; B05B 7/04; B05B 7/0408; B05B 7/0416; B05B 12/00; B05B 12/04; E01H 13/00; A01G 25/16; A01G 25/09; A62C 35/58; A62C 99/0018; A62C 5/002; A62C 3/07; A61L 2/18
USPC .......... 239/1, 8, 14.1, 69, 104, 106, 112, 172, 239/290, 296, 303–305, 311, 419, 422, 433, 239/428; 422/28, 33, 128, 305, 306; 68/5 C; 169/5, 11, 15, 16
See application file for complete search history.

(56) References Cited

U.S. PATENT DOCUMENTS

| | | | | |
|---|---|---|---|---|
| 6,095,251 A | * | 8/2000 | Mitchell et al. ............. | 169/62 |
| 6,841,125 B1 | * | 1/2005 | Chartier et al. ............. | 169/16 |
| 6,898,951 B2 | * | 5/2005 | Severns et al. ............. | 68/5 C |
| 8,062,588 B2 | * | 11/2011 | Sparks et al. ............. | 422/28 |
| 2004/0096354 A1 | * | 5/2004 | Nomura et al. ............. | 422/28 |
| 2010/0218961 A1 | * | 9/2010 | Lade et al. ............. | 169/15 |

* cited by examiner

*Primary Examiner* — Steven J Ganey
(74) *Attorney, Agent, or Firm* — Jeffrey T. Holman

(57) ABSTRACT

A method for multi-agent fogging. The method includes pressurizing a first agent to a first range of pressure. The method also includes pressurizing a second agent to a second range of pressure. The method also includes pressurizing a gas to a gas range of pressure. The method also includes atomizing at least one of the first and second agents at a nozzle to mix with the pressurized gas. The method also includes applying the atomized mixture to fog a space.

**19 Claims

162 Power On Compressors

164 Atomize non-residual fog

166 Atomize cleansing agent

168 Atomize residual fog

172 — Pressurize a first agent to a first range of pressure

174 — Pressurize a second agent to a second range of pressure

176 — Pressurize a gas to a gas range of pressure

178 — Atomize at least one of the first and second agents at a nozzle to mix with the pressurized gas 180 — Apply the atomized mixture to fog a space

ATOMIZING STERILIZATION OF A PLURALITY OF CLEANING AGENTS

CROSS-REFERENCE TO RELATED APPLICATIONS

This application claims the benefit of priority of U.S. Provisional Patent Application 61/494,790 entitled, "ATOMIZING STERILIZATION OF A SEQUENCE OF CLEANING AGENTS" filed on Jun. 8, 2011. The contents of this application are incorporated by reference herein in their entirety.

SUMMARY

According to described embodiments, a method for multi-agent fogging is disclosed. The method includes pressurizing a first agent to a first range of pressure. The method also includes pressurizing a second agent to a second range of pressure. The method also includes pressurizing a gas to a gas range of pressure. The method also includes atomizing at least one of the first and second agents at a nozzle to mix with the pressurized gas. The method also includes applying the atomized mixture to fog a space.

Embodiments of a mobile sterilization system are also described. The system includes an automotive trailer, an atomizing sterilizer apparatus, at least one compressor, and a power source. The automotive trailer facilitates mobility of the mobile sterilization system. The atomizing sterilizer apparatus is coupled to the trailer. The atomizing sterilizer apparatus includes a first reservoir, a second reservoir, a third reservoir, a controller, a manifold, and at least one nozzle. The first reservoir stores a short-term cleaning agent. The second reservoir stores a long-term cleaning agent. The third reservoir stores a rinsing agent. The controller controls an agent quality. The manifold includes at least one connection point for connection of a supply end of a delivery hose. The at least one nozzle is coupled to a delivery end of the delivery hose. The at least one nozzle includes a first inlet, a second inlet, and a discharge point. The first inlet receives a gas at a first range of pressure. The second inlet receives at least one of the short-term and the long-term cleaning agents at a second range of pressure. The discharge point combines the gas and the at least one cleaning agent and atomizes the cleaning agent to produce a dry fog. The at least one compressor is coupled to the trailer. The at least one compressor pressurizes the gas and provides pressure to the atomizing sterilizer apparatus. The power source is coupled to the trailer to provide power to the at least one compressor and to the atomizing sterilizer apparatus.

Embodiments of an apparatus are also described. The apparatus includes a first reservoir, a second reservoir, a third reservoir, and a controller. The first reservoir stores a first cleaning agent. The second reservoir stores a rinsing agent. The third reservoir stores a second cleaning agent. The controller controls sequencing to facilitate a cleaning application sequence in which the first cleaning agent is distributed, the rinsing agent is distributed, and the second cleaning agent is distributed.

Other aspects and advantages of embodiments of the present invention will become apparent from the following detailed description, taken in conjunction with the accompanying drawings, illustrated by way of example of the principles of the invention.

BRIEF DESCRIPTION OF THE DRAWINGS

FIG. 1 depicts a schematic diagram of one embodiment of an atomizing sterilizer system.

FIG. 3 depicts a flow chart diagram of one embodiment of a multi-source atomizing method.

FIG. 8 depicts a flowchart diagram of one embodiment of a method for multi-agent dry fogging.

Throughout the description, similar reference numbers may be used to identify similar elements.

DETAILED DESCRIPTION

Figure 2:
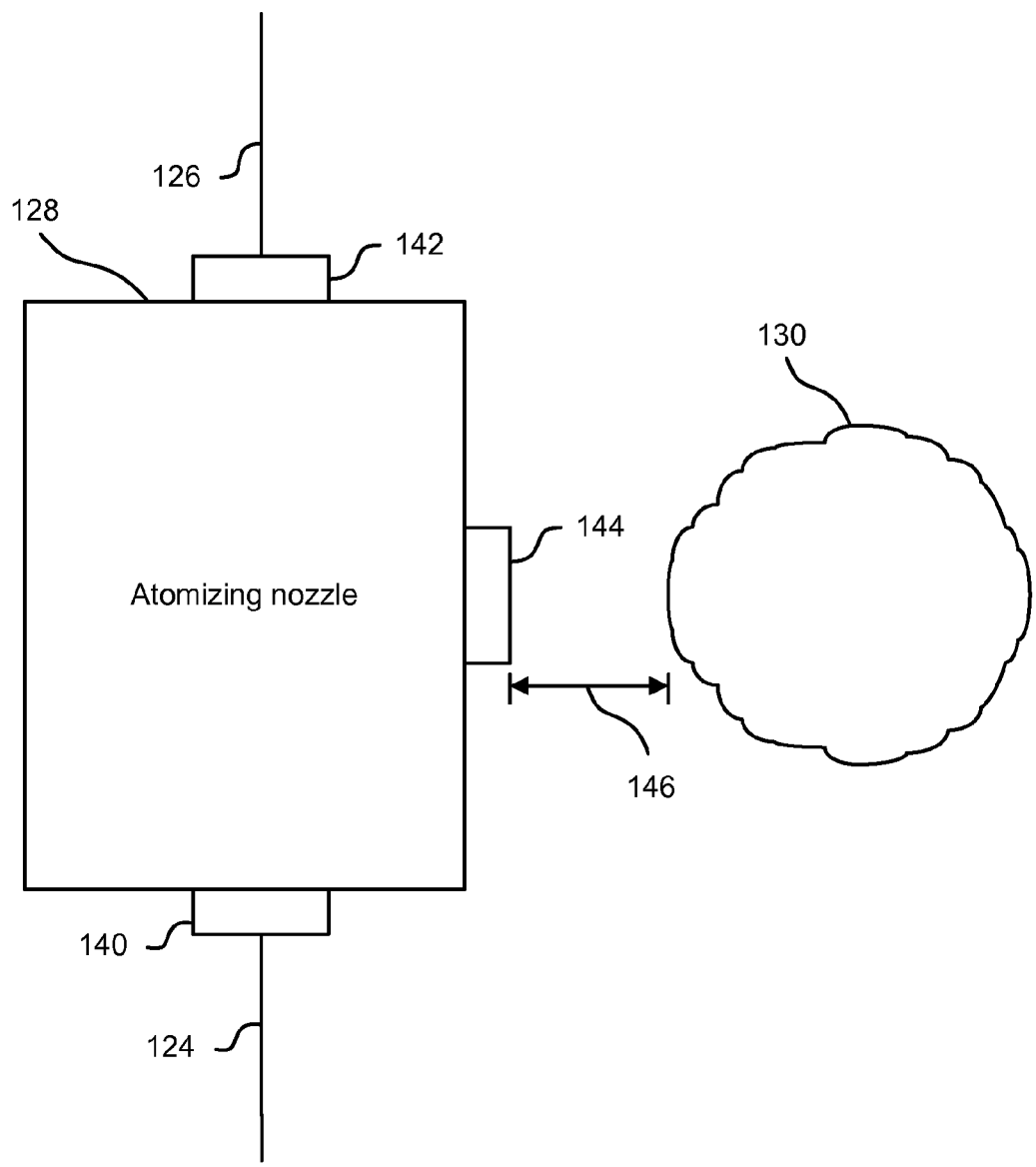
FIG. 2 depicts a schematic diagram of one embodiment of an atomizing nozzle.

It will be readily understood that the components of the embodiments as generally described herein and illustrated in the appended figures could be arranged and designed in a wide variety of different configurations. Thus, the following more detailed description of various embodiments, as represented in the figures, is not intended to limit the scope of the present disclosure, but is merely representative of various embodiments. While the various aspects of the embodiments are presented in drawings, the drawings are not necessarily drawn to scale unless specifically indicated.

The present invention may be embodied in other specific forms without departing from its spirit or essential characteristics. The described embodiments are to be considered in all respects only as illustrative and not restrictive. The scope of the invention is, therefore, indicated by the appended claims rather than by this detailed description. All changes which come within the meaning and range of equivalency of the claims are to be embraced within their scope.

Reference throughout this specification to features, advantages, or similar language does not imply that all of the features and advantages that may be realized with the present invention should be or are in any single embodiment of the invention. Rather, language referring to the features and advantages is understood to mean that a specific feature, advantage, or characteristic described in connection with an embodiment is included in at least one embodiment of the present invention. Thus, discussions of the features and advantages, and similar language, throughout this specification may, but do not necessarily, refer to the same embodiment.

Furthermore, the described features, advantages, and characteristics of the invention may be combined in any suitable manner in one or more embodiments. One skilled in the relevant art will recognize, in light of the description herein, that the invention can be practiced without one or more of the specific features or advantages of a particular embodiment. In other instances, additional features and advantages may be recognized in certain embodiments that may not be present in all embodiments of the invention.

Reference throughout this specification to "one embodiment," "an embodiment," or similar language means that a particular feature, structure, or characteristic described in connection with the indicated embodiment is included in at least one embodiment of the present invention. Thus, the phrases "in one embodiment," "in an embodiment," and similar language throughout this specification may, but do not necessarily, all refer to the same embodiment.

While many embodiments are described herein, at least some of the described embodiments provide an atomizing sterilizer system to sterilize, for a length of time, objects and object surroundings within the target vicinity. In one embodiment, the atomizing sterilizer system utilizes three reservoirs that contain three liquid agents. The three liquid agents are atomized in sequence or simultaneously. The sequence, mixture ratios, and flow rate of the application is managed by a controller. The controller also interfaces with one or more compressors. The compressor supplies gas pressure to the controller. The controller directs the supplied gas pressure to the three reservoirs, as well as to an atomizing nozzle. The sequential application of the cleaning agents is directed into the target vicinity for a period of time. The first agent eliminates most or all of the microorganisms in the vicinity. The second agent rinses the first agent from the atomizing sterilizer system. The third agent is also directed into the target vicinity for a period of time. The third agent adheres to surfaces within the vicinity for a longer period than the first agent. The third agent also continually eliminates most or all of the microorganisms on or around objects in the vicinity. An embodiment of the atomizing sterilizer system provides the benefit of creating a long-term solution for protection against microorganism growth.

Conventional systems may include one system to apply a short-term cleaning agent and another system to apply a long-term cleaning agent. This causes that both systems must be transported to the application site. Additionally, some conventional systems may lack gas pressure in order to more effectively distribute the short-term or long-term cleaning agent. Some conventional systems may require large equipment that may not be transportable to the vicinity to be cleaned. Some conventional systems may not have the ability to be applied in areas with many small rooms, such as residences or small offices, in a reasonable amount of time due to the need to place the system at or near the target vicinity.

Additionally, some conventional systems may emit droplet sizes larger than 10 microns that are less efficient in distributing one or more cleaning agent and that may cause the need to subsequently clean portions in the a vicinity that become dirty, moistened, or damaged due to the larger droplet size of the applied cleaning agent. Additionally, some conventional systems that atomize the agents at particle sizes larger than 10 microns suffer from incomplete spray patterns with open and untreated areas within the spray patterns themselves. Therefore, it is an advantage of the current invention to provide a droplet size smaller than 10 microns to produce a more complete spray pattern and also promote a vapor phase of the agent which greatly increases the effectiveness and efficiency of the agent in application. Further, some systems may not provide full control of one or more pressure values in the application of gases or liquids in conjunction with distribution of the cleaning agent.

Additionally, conventional systems may be incapable of atomizing agents of high viscosity using a Venturi effect or other atomizing method due to the lack of liquid pressure high enough to effectively distribute the highly viscous liquid. Such a configuration makes it impossible to first apply a short-term cleaning agent followed by a long-term cleaning agent or a combination of a short-term cleaning agent and a long-term cleaning agent. Some conventional systems may attempt to distribute a short-term and a long-term cleaning agent simultaneously, resulting in an inability to create a non-wetting dry fog and/or preventing the long-term cleaning agent from bonding to target surfaces.

Figure 1:
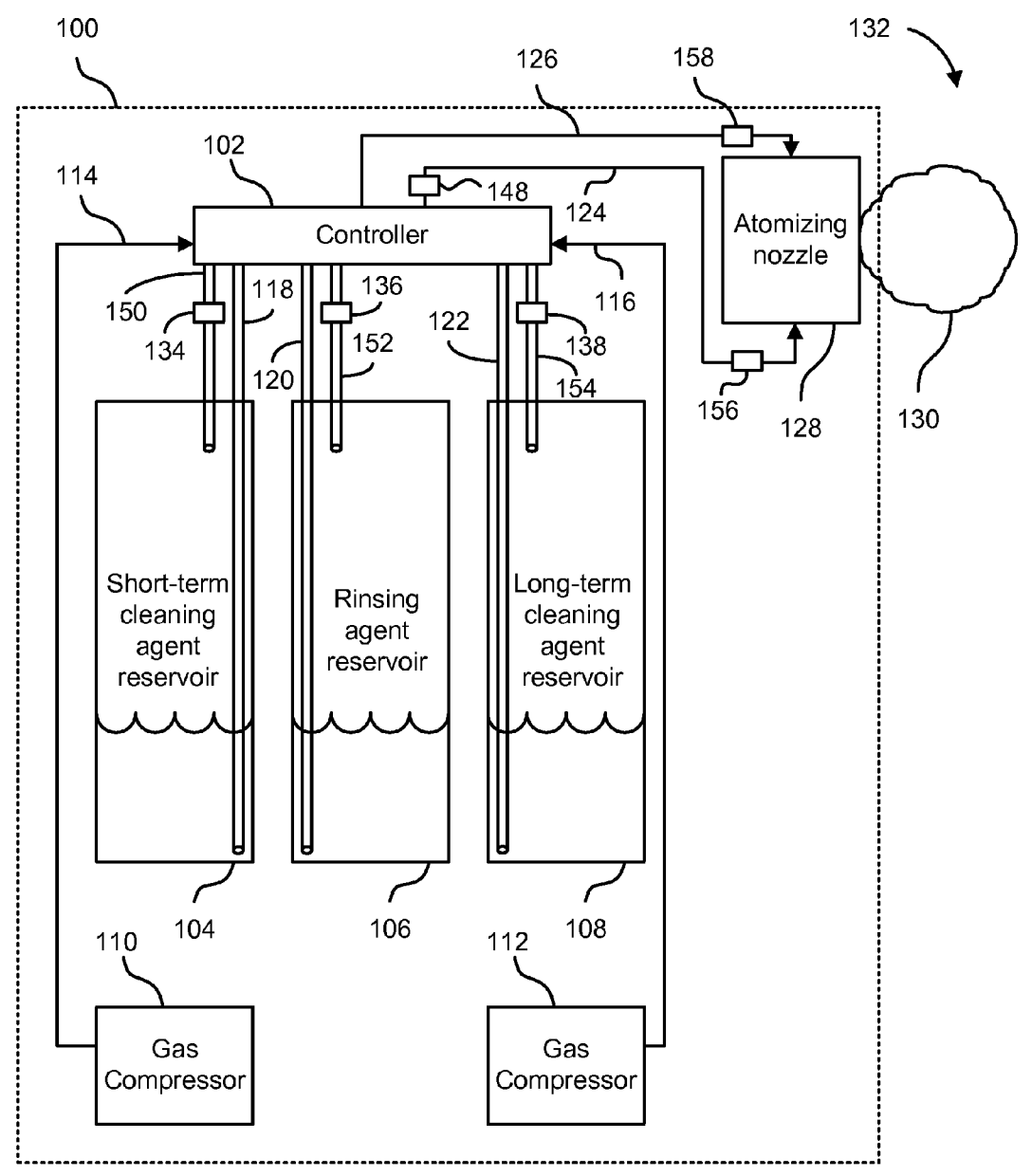

FIG. 1 depicts a schematic diagram of one embodiment of an atomizing sterilizer system 100. The illustrated atomizing sterilizer system 100 includes a controller 102, a short-term cleaning agent reservoir 104, a rinsing agent reservoir 106, and a long-term cleaning agent reservoir 108. The illustrated atomizing sterilizer system 100 also includes gas compressors 110 and 112, gas hoses 114, 116, and 124, liquid hoses 118, 120, 122, and 126, and an atomizing nozzle 128. Although the atomizing sterilizer system 100 is shown and described with certain components and functionality, other embodiments of the atomizing sterilizer system 100 may include fewer or more components to implement less or more functionality.

In one embodiment, the atomizing sterilizer system 100 is used to sterilize, for a length of time, some or all objects and object surroundings located within the target vicinity 132 surrounding the atomizing sterilizer system 100. In an embodiment, a short-term cleaning agent is atomized to create a fog 130. The fog 103 is directed into the target vicinity 132. As the fog 130 comes into contact with microorganisms within the target vicinity 132, some or all of the living microorganisms are disabled or eliminated. The microorganisms are disabled or eliminated by the fog 130 created using the short-term cleaning agent because the short-term cleaning agent contains one or more sterilizing chemicals.

In one embodiment, the short-term cleaning agent is a sterilant, disinfectant, or sanitizing agent. For example, the short-term cleaning agent may be a product known as Insta-Pure. The short-term cleaning agent may be registered with the United States Environmental Protection Agency or another governing body as a sterilant or disinfectant. In one embodiment, the short-term cleaning agent has about 4.5% peracetic (peroxyacetic) acid or more or less than 4.5%. The short-term cleaning agent may also have 22% hydrogen peroxide or more or less than 22%. The short-term agent may also have an oxidizing agent. The short-term cleaning agent may be left within the target vicinity 132 until the hydrogen peroxide air concentration has been verified to be less than or equal to 0.5 ppm or less than or equal to a different threshold value. The short-term cleaning agent may also be left within the target vicinity 132 for 11 hours or more or less than 11 hours. The short-term cleaning agent may also be diluted prior to use. For example, a dilution of one part agent to 99 parts diluted water or more or less than this, may be part of the short-term cleaning agent. The short-term cleaning agent may be applied at 1 to 10 ml of concentrated solution per cubic meter of room volume using a 0.3 to 10% aqueous diluted solution or more or less than this concentration.

Following this atomization, the conduits that carried the short-term cleaning agent are rinsed with a rinsing agent. For example, the rinsing agent may be tap water or purified water. Other embodiments may include a solvent as the rinsing agent.

In an embodiment, a long-term cleaning agent is atomized to create a fog 130. The fog 130 is directed into the target vicinity 132. As the fog 130 comes into contact with objects within the target vicinity 132, some or all of the particles within the fog adhere to the objects. The particles do not deteriorate for a length of time. During this length of time, the particles eliminate most or all of the microorganisms on or around the particles because the particles contain a sterilizing chemical. In one embodiment, this length of time is 90 days or more or less than 90 days. In one embodiment, the length of time is certified by a governing body. In one embodiment, the governing body is the United States Environmental Protection Agency. In one embodiment, the long-term cleaning agent has about 5% by weight or more or less than 5% by weight Silicone Quaternary Ammonium Salt (octadecylaminodimethyltrimethoxysilylpropyl ammonium chloride) or a different compound with substantially similar properties. In one embodiment, the Silicone Quaternary Ammonium Salt is produced by SiShield Technologies, Inc. as a product named SiS AM500. In some embodiments the long-term cleaning agent is a product named EverPure. In one embodiment, the long-term cleaning agent has about 3% by weight or more or less than 3% by weight chloropropyltrimethoxysilane or a compound with substantially similar properties. In one embodiment, the long-term cleaning agent has a high viscosity of about 393 millipascal seconds (mPa s) or greater or lower than 393 millipascal seconds (mPa s). In one embodiment, the long-term cleaning agent is an antimicrobial agent. In an embodiment, the antimicrobial agent is a sterilant, disinfectant, or sanitizing agent. In one embodiment, the long-term cleaning agent disables, denatures, and/or kills at least some microorganisms that may exist within the target vicinity 132 but are not located on an object or surface.

In an embodiment, the long-term cleaning agent has the benefit of long term, or residual protection properties that effectively prevent the growth of microorganisms for a length of time. In some embodiments, the long-term cleaning agent creates an extremely strong bond to the surfaces on to which the agent contacts, such that the long-term cleaning agent does not wipe off. Additionally, in some embodiments, the long-term cleaning agent is non-depleting, and offers substantially the same protection during the entire length of time that the coating remains on the surface. Thus, the atomizing sterilizer system 100 creates a long-term solution for protection against microorganism growth.

The target vicinity 132 may include indoor space, outdoor space, or spaces that are partially indoors and partially outdoors. In one embodiment, the sterilizing of the target vicinity 132 eliminates most or all microorganisms. In other embodiments, the sterilization modifies the composition of one or more microorganisms. However, embodiments herein are not limited to sterilizing. Other embodiments replace or combine the sterilization with disinfecting, sanitation, biocide agents (e.g. pesticides, herbicides, fungicides, etc.), or another cleaning agent.

In the illustrated embodiment, the gas compressors 110 and 112 deliver pressurized gas via the gas hoses 114 and 116. In this way, the gas compressors 110 and 112 may implement functionality to deliver pressurized gas to the controller 102. In another embodiment, a single gas compressor is implemented to provide pressurization to the controller 102 which distributes the pressure to each of the reservoirs 104, 106, and 108 and to the nozzle 128. The controller 102 has a three-way valve. The three-way valve connects to the gas hoses 150, 152, and 154. The gas hoses 150, 152, and 154 are connected to the reservoirs 104, 106, or 108, respectively. Thus, gas can travel from the gas compressors 110 and 112 to the controller 102, then to the gas hoses 150, 152, and 154, then to the reservoirs 104, 106, or 108, respectively, in order to pressurize the contents of the reservoirs 104, 106, or 108. In other embodiments, the three-way valve of the controller 102 is replaced with a combination of valves, tees, and/or couplings. In other embodiments, the controller 103 has other types of valves, tees, or couplings. In some embodiments, the controller 102 includes a manifold to facilitate connection of multiple nozzles 128 to deliver treatment to multiple target areas 132 simultaneously. In some embodiments, the controller 102 includes a sensor such as a programmable logic circuit to monitor qualities of the agents and treatment. For example, the sensor may measure concentration, application duration (time of delivery), temperature, pressure, flow rate, humidity, reservoir fill level, etc. In one embodiment, the sensor is configured to verify that the short-term cleaning agent is delivered at a rate of 1.5 ml/m$^3$ and the long-term cleaning agent is delivered at a gal./10,000 ft$^2$. If the sensor detects that one of these qualities as being below a certain level or standard, the sensor will respond by initiating an auto-shut-off. In some embodiments the sensor may provide for a delay during a rinsing stage or control a heating or refrigeration element coupled to the agent reservoirs 104, 106, or 108. In some embodiments, the sensor is configured to verify that between 3-3.5 cfm is delivered to each nozzle 128. The sensor may also monitor backflow into the reservoirs 104, 106, or 108 to prevent mixing or detects malfunctions. In other embodiments, the pressurized gas is delivered to one or more reservoirs 104, 106, or 108. In one embodiment, the pressure range of the compressor 110 is different from the pressure range of the compressor 112. In other embodiments, the compressor pressure range is substantially the same in both compressors 110 and 112. In one embodiment, one or more of the compressors 110 or 112 outputs a large mass flow in comparison to other similar compressors. In other embodiments, the mass flow is normal or smaller than similar compressors. The compressors 110 and 112 may be replaced or combined with fewer or more compressors. Additionally, in other embodiments, the gas is replaced or combined with other gases.

In one embodiment, the gas pressure regulator 134 is located along gas hose 150 in order to deliver the gas pressure to reservoir 104 at a range of about 12-15 pounds per square inch gauge (PSIG). In other embodiments, the gas pressure is delivered at a range of about 10-20 PSIG. In other embodiments, the gas pressure is at a range of about 1-50 PSIG. In other embodiments, the gas pressure is more or less than the above-described ranges. In some embodiments, one gas pressure regulator controls the pressure of more than one gas hose. For example, in one embodiment, the same gas pressure regulator could be used to control the pressure delivered to reservoir 104 and reservoir 106.

In one embodiment, the gas pressure regulator 136 is located along the gas hose 152 in order to deliver the gas pressure to reservoir 106 at a range of about 12-15 pounds per square inch gauge (PSIG). In other embodiments, the gas pressure is delivered at a range of about 10-20 PSIG. In other embodiments, the gas pressure is at a range of about 1-50 PSIG. In other embodiments, the gas pressure is more or less than the above-described ranges.

In one embodiment, the gas pressure regulator 138 is located along the gas hose 154 in order to deliver the gas pressure to the reservoir 108 at a range of about 18-20 pounds per square inch gauge (PSIG). In other embodiments, the gas pressure is delivered at a range of about 15-25 PSIG. In other embodiments, the gas pressure is at a range of about 1-50 PSIG. In other embodiments, the gas pressure is more or less than the above-described ranges.

In one embodiment, the gas is simply air or air combined with other gases. In one embodiment, the air pressure regulator 148 is located somewhere along the gas hose 124 in order to deliver the gas pressure to the atomizing nozzle 128 at a controllable pressure. In one embodiment, the gas is pressurized about 70 PSIG or more or less than 70 PSIG.

In one embodiment, the short-term cleaning agent reservoir 104 stores the short-term cleaning agent in a liquid form. The short-term cleaning agent 104 may be transferred to the controller 102 via the liquid hose 118 and to the atomizing nozzle 128 via the liquid hose 126. In one embodiment, a simultaneous flow of gas from the compressor 110 travels via the gas hose 114 to the controller 102, then via the gas hose 124 to the atomizing nozzle 128. In one embodiment, the gas hose 124 bypasses the controller and is connected directly to one or more gas compressors. In an embodiment, the gas from the compressor 110 is combined with the short-term cleaning agent at or near the atomizing nozzle 128 to create an atomized agent. Additionally, in one embodiment, the short-term cleaning agent reservoir 104 interfaces with the gas compressor 110 via the gas hose 114 in order to send, via compressed gas pressure, the contents of the short-term cleaning agent reservoir 104 to the controller 102. In one embodiment, the control valves 156 and 158 control the flow within the hoses 124 and 126, respectively. The control valves 156 and 158 may be capable of stopping the flow of the hoses 124 and 126. The control valves 156 and 158 may be variable, ball, needle, or another type of valve.

In one embodiment, the rinsing agent reservoir 106 stores a rinsing agent in a liquid form. The rinsing agent reservoir 106 may be transferred to the controller 102 via the liquid hose 122 and to the atomizing nozzle 128 via the liquid hose 126. In an embodiment, gas from the compressor 110 or 112 via the controller 102 and the rinsing agent are combined at or near the atomizing nozzle 128 to create an atomized agent. In other embodiments, the rinsing agent is not atomized or is only partially atomized. The rinsing agent may be water or another chemical necessary to effectually rinse existing agents in the atomizing sterilizer system 100. Additionally, in one embodiment, the rinsing agent reservoir 106 interfaces with the gas compressor 110 or 112 via the controller 102 in order to send, via compressed gas pressure, the contents of the rinsing agent reservoir 106 to the controller 102. In an embodiment, the rinsing agent flushes the short-term cleaning agent partially or completely from some or all components of the atomizing sterilizer system 100. In other embodiments, the rinsing agent flushes the long-term cleaning agent, or other agents, in the atomizing sterilizer system 100, either partially or completely from some or all components of the atomizing sterilizer system 100.

In some embodiments, the rinsing agent reservoir 106 is implemented within the atomizing sterilizer system 100 to provide certain advantages over conventional technologies. For example, some embodiments of the atomizing sterilizer system 100 implement the rinsing agent reservoir 106 to enable a complex sterilizing solution by allowing more than one agent to be applied in sequence. Additionally, the application of agents in sequence, rather than simultaneous application, assures that each agent is applied in an effective manner without interference from other agents. For example, the short-term cleaning agent is allowed to substantially dry before the application of the long-term cleaning agent, thus preventing any wetness in the long-term cleaning agent, thus also preventing loss of adhesion, as described in conventional systems, above. In another embodiment, the short-term cleaning agent is allowed to remain within the target vicinity 132 long enough so that the short-term cleaning agent does not interfere with the cleaning action of the long-term cleaning agent. In another embodiment, the short-term cleaning agent is allowed to remain within the target vicinity 132 long enough so that the long-term cleaning agent will not interfere with the cleaning action of the short-term cleaning agent. In other embodiments, the rinsing agent cleans existing agents that may deteriorate, corrode, clog, or make more inefficient or ineffective a portion of the atomizing sterilizer system 100. In other embodiments, the rinsing agent enables the droplet size to be controlled more closely for a longer period of time. In other embodiments, the atomizing sterilizer system 100 implements the rinsing agent reservoir 106 in order to rinse some or all components of the atomizing sterilizer system 100 without further application of a second agent. In other embodiments, substantially the same cleaning agent is applied following rinsing. Additionally, more than two agents are applied, while one or more of the agent applications are followed by a flush of the rinsing agent. In one embodiment, the rinsing agent is applied before the first cleaning agent is applied. Embodiments of the atomizing sterilizer system 100 may implement the rinsing agent reservoir 106 to achieve other advantages. Additionally, embodiments allow agents of a high viscosity to be atomized with the aid of pressurized gas.

In one embodiment, the atomizing sterilizer system 100 can remain transported via vehicle or trailer and delivered to the target vicinity 132 via extended versions of the hoses 124 and 126. In one embodiment, the control valves 156 and 158 may be situated near the end of the hoses 124 and 126 that connect to the atomizing nozzle 128 in order to allow control of air and gas flow near the target vicinity 132. This configuration provides the advantage of rapid application at the target vicinities 132 because the atomizing sterilizer system 100 need not be located in, or even close to, the target vicinity 132. For example, the atomizing sterilizer system 100 need not be transported during application to multiple apartments, multiple rooms within a residence, multiple residences, multiple commercial structures, multiple rooms within commercial structures, areas above or below structures, other structures, or outdoor environments. Additionally, the atomizing nozzle 128 can reach entrances to HVAC (Heating, Ventilating, and Air Conditioning) or other systems in order to sterilize the system. Additionally, the atomizing sterilizer system 100 can be transported to a new location at a faster pace, and with less effort, than systems where the sterilizer system must be carried to or near the application site. Additionally, the atomizing sterilizer system 100 is easily set up (usually in around 15 mins.). The system can be trailer mounted and parked at a location with hoses to deliver the agents to the target area. The atomizing sterilizer system 100 is especially advantageous in situations such as treatment of an area to denature methamphetamines. In order to denature an area exposed to meth, the delivery of each agent must be rapid and thorough. The described atomizing sterilizer system 100 is capable of such a treatment.

In one embodiment, the long-term cleaning agent reservoir 108 stores a long-term cleaning agent in a liquid form. In this way, the long-term cleaning agent reservoir 108 may implement functionality to be transferred to the controller 102 via the liquid hose 122 and to the atomizing nozzle 128 via the liquid hose 126. In one embodiment, a simultaneous flow of gas from the compressor 112 travels via the gas hose 116 to the controller 102, then via the gas hose 124 to the atomizing nozzle 128. In an embodiment, the gas from the compressor 112 and the long-term cleaning agent are combined at or near the atomizing nozzle 128 to create an atomized agent. Additionally, in one embodiment, the long-term cleaning agent reservoir 108 interfaces with the gas compressor 112 via the gas hose 116 in order to send, via compressed gas pressure, the contents of the long-term cleaning agent reservoir 108 to the controller 102.

In some embodiments, the short-term cleaning agent reservoir 104 and long-term cleaning agent reservoir 108 are implemented within the atomizing sterilizer system 100 to provide certain advantages over conventional technologies.

For example, some embodiments of the atomizing sterilizer system 100 implement the short-term cleaning agent as a precursor to the long-term cleaning agent increase the effectiveness of the long-term cleaning agent. In one embodiment, the effectiveness of the long-term cleaning agent is improved because the short-term cleaning agent disables, denatures, and/or kills some or all microorganisms in some or all of the surfaces and/or surrounding environment of the target vicinity 132. In other embodiments, the order of application of the short- and long-term agents is reversed. In further embodiments, any combination of the three reservoir agents can be simultaneously applied, applied multiple times, or omitted from the application sequence.

In one embodiment the controller 102 controls the sequencing of cleaning or rinsing agent applications. In some embodiments, the controller 102 contains additional hoses, valves, or connectors, as well as additional mechanisms for extracting agents from the reservoirs 104, 106, and 108 or propelling the agents away from the controller 102. In other embodiments, some or all of the cleaning or rinsing agents are in the form of a liquid. In other embodiments, some or all of the cleaning or rinsing agents are a liquid, solid, gas, or combination of these. In one embodiment, one or more of the cleaning or rinsing agents are omitted from the sequence, or combined with other liquids, solids, gases, or combination of these. For example, the target vicinity 132 may be physically cleaned by the atomizing sterilizer system or another system previous to, during, or after the above-described applications. In some embodiments, the controller 102 adds or uses pressure to extract or propel the cleaning or rinsing agent. Another embodiment uses a Venturi effect to extract or propel the cleaning or rinsing agent. In some embodiments, the efficacy of any or all of the above-described applications is validated by some means.

In one embodiment, the gas hoses 114, 116, and 124 and the liquid hoses 118, 120, 122, and 126 are hoses that carry, respectively, gas and liquid from one component to the next. In some embodiments, the hoses are combined with other hoses, couplings, valves, or connectors. In other embodiments, the hose is replaced with pipes, couplings, other connectors, or simply holes from one component to the next.

FIG. 2 depicts a schematic diagram of one embodiment of an atomizing nozzle 128. The illustrated atomizing nozzle 128 includes the inlet 140 that interfaces with the gas hose 124, the inlet 142 that interfaces with the liquid hose 126, and the outlet 144. Although the atomizing nozzle 128 is shown and described with certain components and functionality, other embodiments of the atomizing nozzle 128 may include fewer or more components to implement less or more functionality.

In one embodiment, the atomizing nozzle 128 directs gas from the inlet 140 to create one or more streams of gas, while also directing liquid from the inlet 142 to create one or more streams of liquid, some or all of which interact with the one or more gas streams to create fog 130 of the liquid and gas. The fog 130 travels from the atomizing nozzle 128 at the outlet 144. In one embodiment, the mean diameter of particles within the fog 130 is between 1 and 10 microns. In another embodiment, the mean diameter of the particles within the fog 130 is between 1 and 15 microns. In other embodiments, a larger or smaller mean size of particles within the fog may be achieved. In other embodiments, more than one liquid and/or more than one gas may be combined to be partially or completely atomized at the atomizing nozzle 128. In some embodiments, the atomization occurs within the atomizing nozzle 128. In other embodiments, the liquid and or the gas travel outside of the atomizing nozzle 128 for some distance 146 before the atomization occurs. In further embodiments, more than one outlet or different mechanisms for atomization exists.

In some embodiments, the liquid is delivered using positive pressure or pressure from the liquid hose 124. In other embodiments, the liquid is replaced or combined with another liquid, solid, gas, or combination of these. In some embodiments, the atomizing nozzle 128 or other non-nozzle mechanism operates via rotary, pressure, two-fluid combination, thermal energy, or electrical impulse components in order to create atomized particles. Other atomization protocols may be used in the atomizing nozzle 128. In some embodiments, the atomizing nozzle 128 draws liquid by using the Venturi effect to extract or propel the emerging liquid.

In one embodiment, the pressure applied at the atomizing nozzle 128 is about 50 PSIG gas and about 10 PSIG liquid. In another embodiment, the gas pressure is within a range of about 10 PSIG above or below about 50 PSIG. In another embodiment, the liquid pressure is within a range of about 5 PSIG above or below 10 PSIG. In another embodiment, the gas pressure is any value less than about 20 PSIG. In another embodiment, the liquid pressure is any value greater than about 35 PSIG.

In other embodiments, the pressure is different for some or all applications of the agent of each reservoir 104, 106, and 108. Additionally, the pressure may be absent for one or more atomizing nozzle 128 inlet hoses. In some embodiments, the pressure is varied in a pulse pattern. In some embodiments, the atomized agent emits directly into the target vicinity 132. In other embodiments, a hose or other component is used to direct the atomized agent to a specific location away from the atomizing nozzle 128. The atomized material may propel into the target vicinity 132 via momentum from the pressure used to atomize the agent. The atomized agent further distributes via random molecule motion within the target vicinity 132. In other embodiments, other mechanisms are used to distribute the atomized agent. For example, some embodiments of the atomized sterilizer system may implement other sources of energy to produce air flow within the target vicinity 132 in order to more efficiently or effectively distribute the atomized agent.

In some embodiments, the atomizing nozzle 128 is implemented within the atomizing sterilizer system 100 to provide certain advantages over conventional technologies. For example, some embodiments of the atomizing sterilizer system 100 implement the atomizing nozzle 128 to create a fog 130. The fog 130 may be a dry fog, which has the advantage of further reach to otherwise unreachable portions of the target vicinity 132. Additionally, a dry fog provides the further advantage of preventing wetting and deterioration of objects within the target vicinity 132. Other embodiments of the atomizing sterilizer system 100 may implement the atomizing nozzle 128 to create a wet fog, other gas, liquid, solid, or a combination of these, in order to achieve the desired short- or long-term microorganism control solution.

FIG. 3 depicts a flow chart diagram of one embodiment of a multi-source atomizing method 160. At block 162, the sequence is initiated with the powering on of one or both compressors 110 and 112. In other embodiments, no compressor is necessary and this block is not part of the method.

At block 164, the short-term cleaning agent is then delivered via liquid hose 118 from short-term cleaning agent reservoir 104 to the controller 102, then via the liquid hose 126 to the atomizing nozzle 128. The short-term cleaning agent is then atomized for a period of time at a pre-determined pressure range. At block 166, a rinsing agent is then delivered via the liquid hose 120 from the rinsing agent reservoir 106 to the controller 102, then via the liquid hose 126 to the atomizing nozzle 128 for a period of time. In some embodiments, the rinsing agent is atomized for a period of time at a pre-determined pressure range. At block 168, the long-term cleaning agent is then delivered via the liquid hose 122 from the short-term cleaning agent reservoir 104 to the controller 102, then via the liquid hose 126 to the atomizing nozzle 128. The long-term cleaning agent is then atomized for a period of time at a pre-determined pressure range. Other embodiments rearrange the order of sequence, repeating or omitting some sequence blocks.

Figure 4:
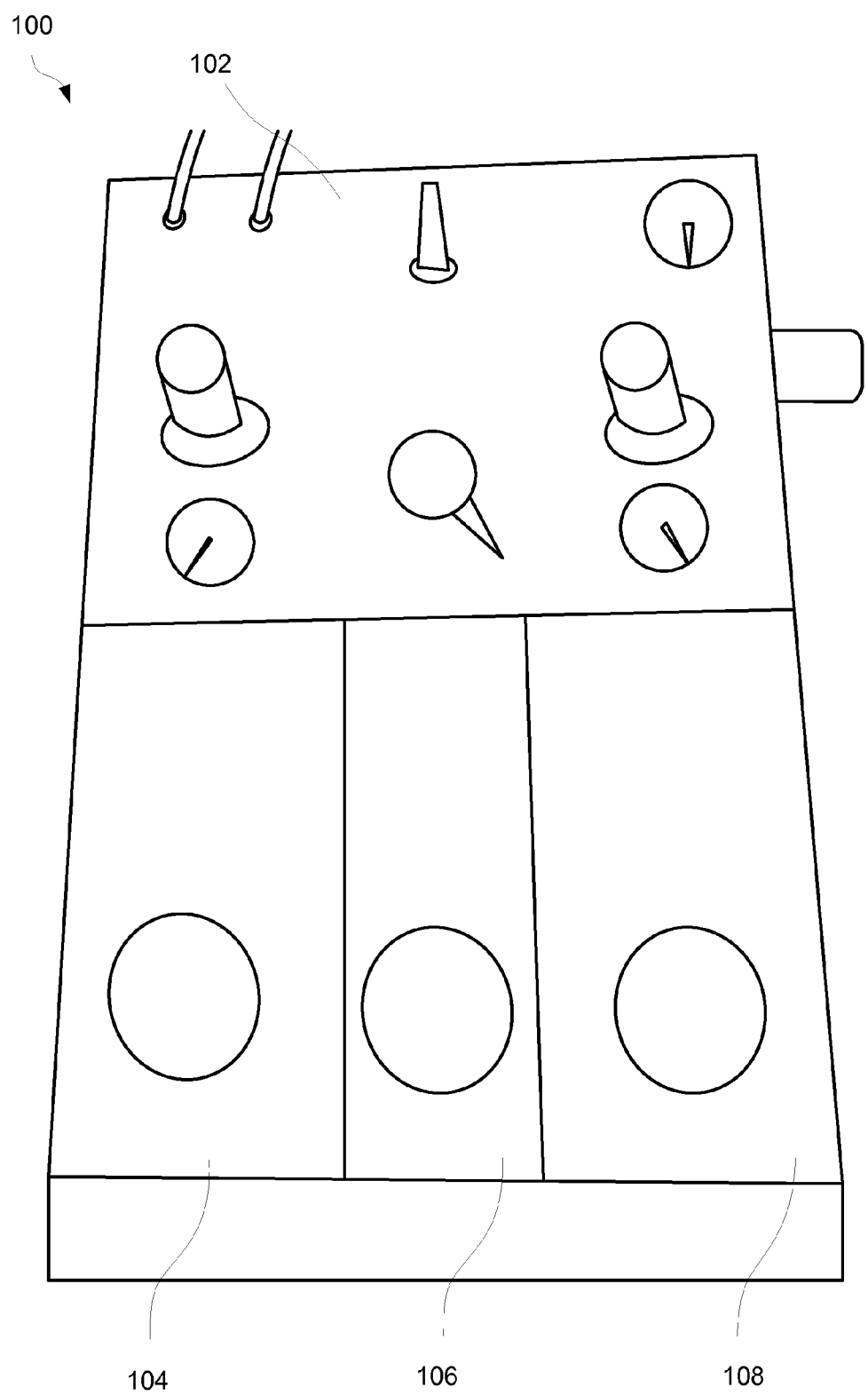
FIG. 4 depicts one embodiment of an atomizing sterilizer system.
Figure 5:
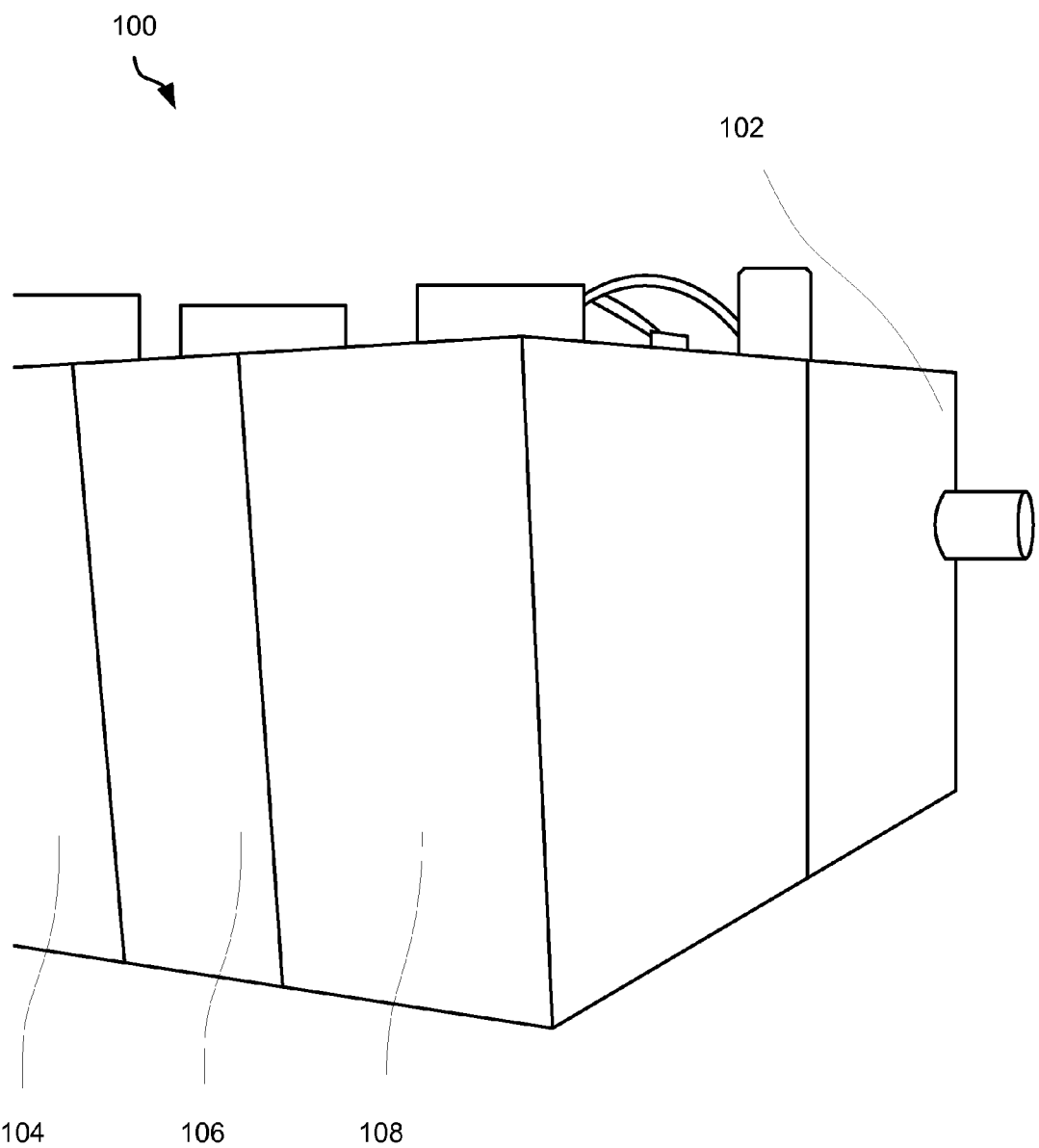
FIG. 5 depicts another embodiment of the atomizing sterilizer system of FIG. 4.
Figure 6:
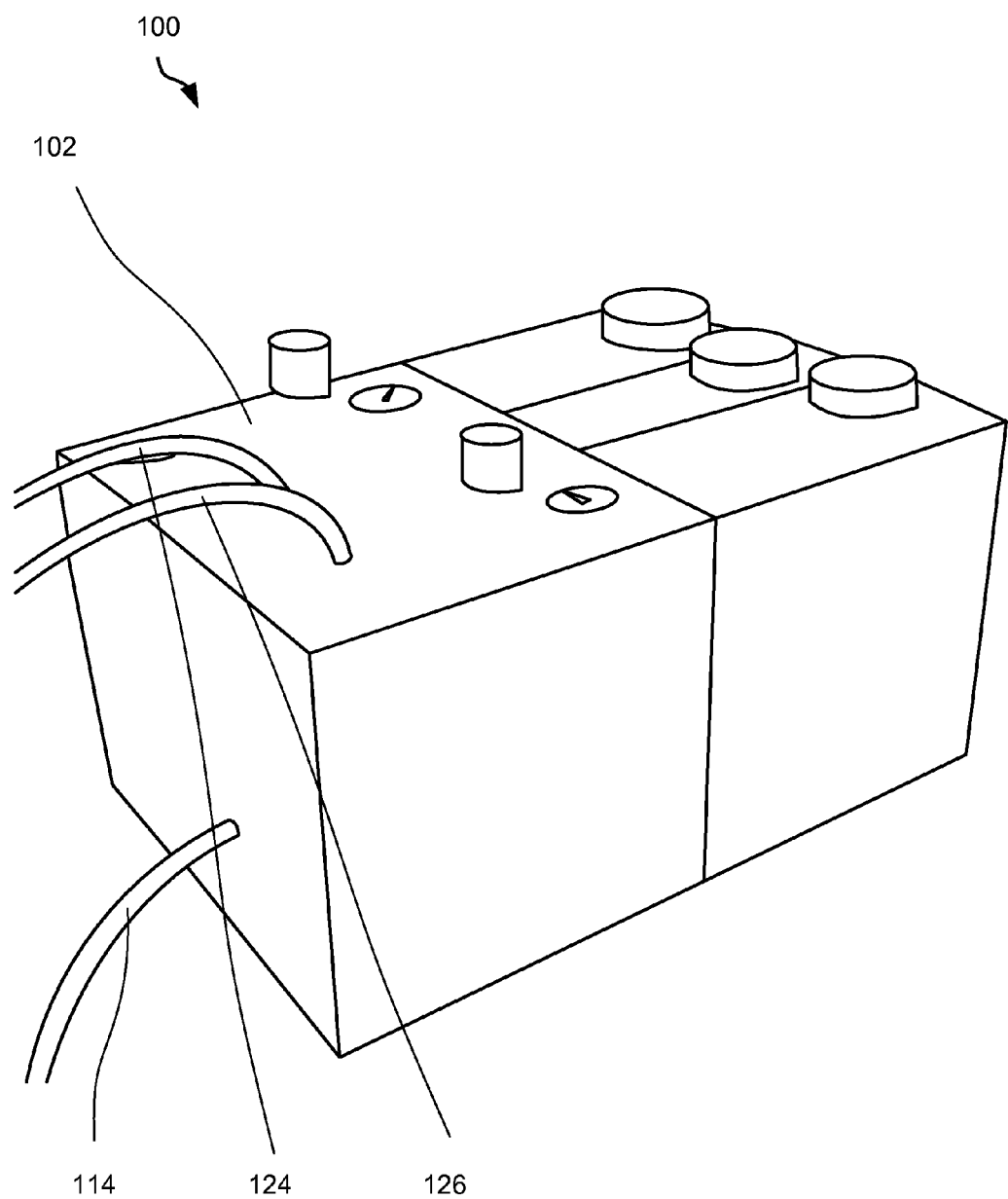
FIG. 6 depicts another embodiment of the atomizing sterilizer system of FIG. 4.

FIGS. 4-6 depict one embodiment of an atomizing sterilizer system 100. The illustrated atomizing sterilizer system 100 contains a controller 102, a short-term cleaning agent reservoir 104, a rinsing agent reservoir 106, and a long-term cleaning agent reservoir 108. The controller 102 includes necessary gauges, controls, inlets, and outlets in order to accomplish the functions of atomizing sterilizer system 100. Although the atomizing sterilizer system 100 is shown and described with certain components and functionality, other embodiments of the atomizing sterilizer system 100 may include fewer or more components to implement less or more functionality.

The illustrated atomizing sterilizer system 100 provides certain advantages over conventional technologies. For example, the atomizing sterilizer system 100 can be carried directly into the target vicinity without aid of a cart, vehicle, etc. while still being enabled to deliver a sequence of atomized cleaning agents to the target vicinity 132. The atomizing sterilizer system 100 is also able to distribute atomized agent into the target vicinity 132 with much greater efficiency than conventional atomizing cleaning agent distribution systems due to the ability to control pressure of the above-described pressurized gas.

Figure 7:
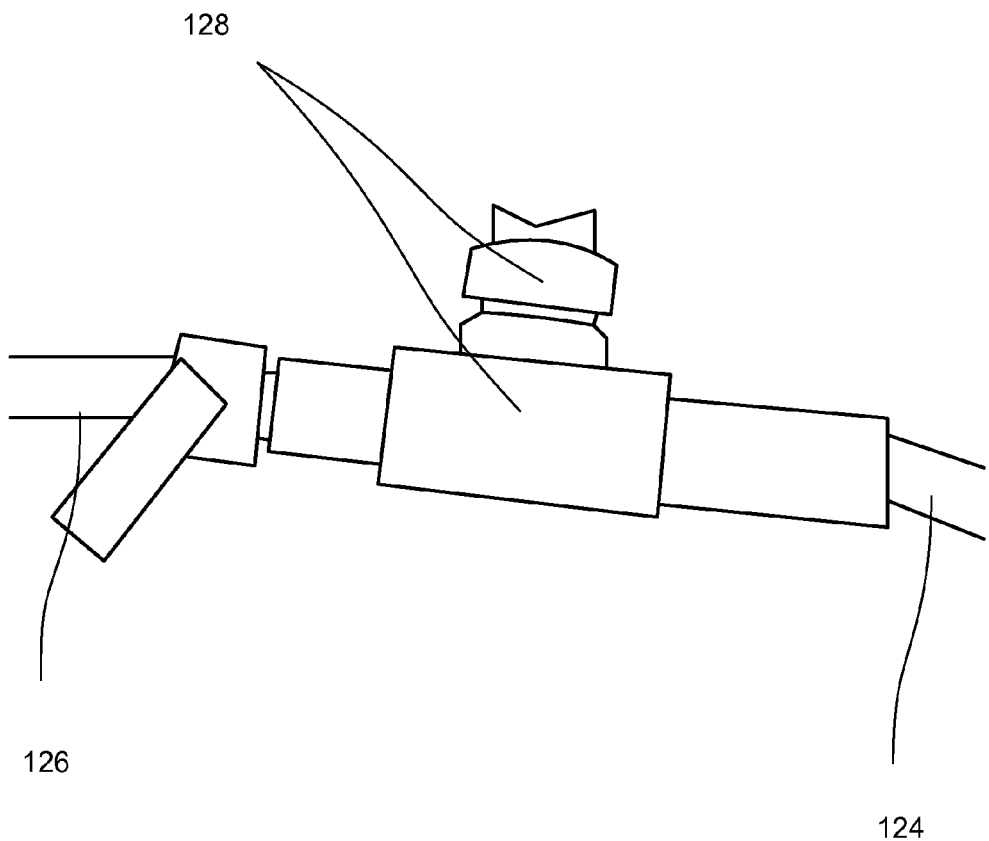
FIG. 7 depicts one embodiment of an atomizing nozzle.

FIG. 7 depicts one embodiment of an atomizing nozzle 128, Spraying Systems Co. model 1/4J-1650-67228-45. Although the atomizing nozzle 128 is shown and described with certain components and functionality, other embodiments of the atomizing nozzle 128 may include fewer or more components to implement less or more functionality. Additionally, other atomizing mechanisms may replace or combine with an atomizing nozzle 128.

The atomizing nozzle 128 in the FIG. 7 receives pressurized cleaning agent in the form of a liquid or rinsing agent in the form of a liquid from liquid hose 126 of FIG. 7. The atomizing nozzle 128 of FIG. 7 directs pressurized gas from gas hose 124 of FIG. 7, through the atomizing nozzle 128, and out of two holes. The center axis of each hole may be configured at approximately 90 degrees to the center axis of the other hole, such that the streams from each hole collide at a center axis. The atomizing nozzle 128 of FIG. 7 also directs the pressurized liquid through the atomizing nozzle 128 and out along the center axis. The liquid collides with two streams of air, which ongoing collision provides a constant flow of dry fog that flows, due to the gas and liquid pressure and possibly other forces, into the target vicinity 132 of FIG. 7. Additional embodiments may use different configurations or quantities of the above-described holes and nozzle structures.

The atomizing nozzle 128 in FIG. 7 provides certain advantages over conventional technologies. For example, some embodiments of the atomizing nozzle 128 of FIG. 7 implement an optimized liquid pressure and optimized gas pressure for each agent that allow for a faster completion of the delivery of the various atomized agents distributed by the atomizing sterilizer system 100.

FIG. 8 depicts a flowchart diagram of one embodiment of a method 170 for multi-agent dry fogging. The method 170 includes pressurizing 172 a first agent to a first range of pressure. The method 170 also includes pressurizing 174 a second agent to a second range of pressure. The method 170 also includes pressurizing 176 a gas to a gas range of pressure. The method 170 also includes atomizing 178 at least one of the first and second agents at a nozzle to mix with the pressurized gas. The method 170 also includes applying 180 the atomized mixture to fog a space.

In the above description, specific details of various embodiments are provided. However, some embodiments may be practiced with less than all of these specific details. In other instances, certain methods, procedures, components, structures, and/or functions are described in no more detail than to enable the various embodiments of the invention, for the sake of brevity and clarity.

Although the operations of the method(s) herein are shown and described in a particular order, the order of the operations of each method may be altered so that certain operations may be performed in an inverse order or so that certain operations may be performed, at least in part, concurrently with other operations. In another embodiment, instructions or sub-operations of distinct operations may be implemented in an intermittent and/or alternating manner.

Although specific embodiments of the invention have been described and illustrated, the invention is not to be limited to the specific forms or arrangements of parts so described and illustrated. The scope of the invention is to be defined by the claims appended hereto and their equivalents.

What is claimed is:

1. A method for multi-agent dry fogging, the method comprising:
   pressurizing a first agent to a first range of pressure;
   pressurizing a second agent to a second range of pressure;
   pressurizing a gas to a gas range of pressure;
   atomizing at least one of the first and second agents at a nozzle to mix with the pressurized gas;
   applying the atomized mixture to fog a space, wherein the first agent is applied for a first application duration and the second agent is applied for a second application duration;
   rinsing out a remnant of at least one of the first and second agents; and
   switching to select a function of atomizing the first agent, atomizing the second agent, atomizing both the first and second agents, or rinsing out the remnant of at least one of the first and second agents.

2. The method of claim 1, wherein the first agent is atomized with the gas in a first application stage and the second agent is atomized with the gas in a second application stage.

3. The method of claim 2, further comprising delaying for a time between the first application stage and the second application stage.

4. The method of claim 1, wherein applying the atomized mixture comprises calculating a volume of the atomized mixture based on a dimension of the space.

5. The method of claim 1, wherein at least one of the first agent, second agent, or a rinsing agent is maintained between approximately 50° F. and 80° F.

6. The method of claim 1, further comprising supplying 3-3.5 ft$^3$/minute to each of a plurality of atomization nozzles, the plurality of atomization nozzles to facilitate multiple application points.

7. The method of claim 1, further comprising monitoring at least one of a plurality of qualities, the plurality of qualities comprising agent concentration, application duration, temperature, pressure, flow rate, humidity, and reservoir fill level, and initiating an auto-shut-off in response to a determination that at least one of the plurality of qualities is insufficient.

8. The method of claim 1, wherein:
   the first agent comprises a sterilant; and
   the second agent comprises a non-depleting solution for protection against microorganism growth.

9. A mobile sterilization system comprising:
   an automotive trailer to facilitate mobility of the mobile sterilization system;
   an atomizing sterilizer apparatus coupled to the automotive trailer, wherein the atomizing sterilizer apparatus comprises:

a first reservoir to store a short-term cleaning agent;
a second reservoir to store a long-term cleaning agent;
a third reservoir to store a rinsing agent;
a controller to control an agent quality;
a manifold comprising at least one connection point for connection of a supply end of a delivery hose; and
at least one nozzle coupled to a delivery end of the delivery hose, the at least one nozzle comprising:
a first inlet to receive a gas at a first range of pressure;
a second inlet to receive one or more of the cleaning agents at a second range of pressure; and
a discharge point to combine the gas and the one or more leaning agents and atomize the one or more cleaning agents to produce a dry fog;
at least one compressor coupled to the automotive trailer, the at least one compressor to pressurize the gas and provide pressure to the atomizing sterilizer apparatus; and
a power source coupled to the automotive trailer to provide power to the at least one compressor and to the atomizing sterilizer apparatus.

10. The mobile sterilization system of claim 9, wherein the at least one nozzle is further configured to atomize the one or more cleaning agents to a mean particle diameter between 1 micron and 10 microns.

11. The mobile sterilization system of claim 9, wherein the at least one nozzle is further configured to atomize the one or more cleaning agents to a mean particle diameter between 1 micron and 15 microns.

12. The mobile sterilization system of claim 9, wherein the one or more cleaning agents is an antimicrobial agent.

13. The mobile sterilization system of claim 9, wherein:
the first range of pressure is between about 40 pounds per square inch (PSI) and about 60 PSI; and
the second range of pressure is between about 5 pounds per square inch (PSI) and about 15 PSI.

14. The mobile sterilization system of claim 9, wherein:
the first range of pressure is about 50 PSI; and
the second range of pressure is about 10 PSI.

15. A method for multi-agent dry fogging, the method comprising:
pressurizing a first agent to a first range of pressure;
pressurizing a second agent to a second range of pressure;
pressurizing a gas to a gas range of pressure;
atomizing at least one of the first and second agents at a nozzle to mix with the pressurized gas;
applying the atomized mixture to fog a space;
rinsing out a remnant of at least one of the first and second agents; and
switching to select a function of atomizing the first agent, atomizing the second agent, atomizing both the first and second agents, or rinsing out the remnant of at least one of the first and second agents.

16. The method of claim 15, wherein the first agent is atomized with the gas in a first application stage and the second agent is atomized with the gas in a second application stage, wherein the method further comprises delaying for a time between the first application stage and the second application stage.

17. The method of claim 15, wherein at least one of the first agent, second agent, or a rinsing agent is maintained between approximately 50° F. and 80° F.

18. The method of claim 15, further comprising monitoring at least one of a plurality of qualities, the plurality of qualities comprising agent concentration, application duration, temperature, pressure, flow rate, humidity, and reservoir fill level, and initiating an auto-shut-off in response to a determination that at least one of the plurality of qualities is insufficient.

19. The method of claim 15, wherein:
the first agent comprises a sterilant; and
the second agent comprises a non-depleting solution for protection against microorganism growth.

* * * * *